United States Patent
López et al.

(10) Patent No.: US 10,689,380 B1
(45) Date of Patent: Jun. 23, 2020

(54) CRYSTALLINE FORMS OF VALBENAZINE DITOSYLATE

(71) Applicant: Farmhispania S.A., Barcelona (ES)

(72) Inventors: Rafel Prohens López, Sabadell (ES); Raquel Cordobilla Cascales, Badalona (ES); Xavier Pujol Ollé, Barcelona (ES); Óscar Martínez Pérez, Terrassa (ES)

(73) Assignee: Farmhispania S.A., Barcelona (ES)

( * ) Notice: Subject to any disclaimer, the term of this patent is extended or adjusted under 35 U.S.C. 154(b) by 0 days.

(21) Appl. No.: 16/525,998

(22) Filed: Jul. 30, 2019

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
See application file for complete search history.

(56) References Cited

U.S. PATENT DOCUMENTS

| 8,039,627 B2 | 10/2011 | Gano |
| 10,065,952 B2 * | 9/2018 | McGee ................ C07D 471/04 |

FOREIGN PATENT DOCUMENTS

| EP | 3473623 A1 | 4/2019 |
| WO | 2018067945 A1 | 4/2018 |
| WO | 2018130345 A1 | 7/2018 |
| WO | 2018153632 A1 | 8/2018 |
| WO | 2019129100 A1 | 4/2019 |
| WO | 2019104141 A1 | 5/2019 |

* cited by examiner

*Primary Examiner* — Timothy R Rozof
(74) *Attorney, Agent, or Firm* — Green, Griffith & Borg-Breen LLP

(57) ABSTRACT

Disclosed herein are new crystalline forms of valbenazine ditosylate designated Form D and Form E, which are characterized using one or more analytical methods, such as X-ray Powder Diffraction analysis. Further disclosed herein are crystalline Form D valbenazine ditosylate in the form of a dichloromethane solvate, and crystalline Form E valbenazine ditosylate in the form of a hydrate. Also disclosed are pharmaceutical compositions comprising these new crystalline forms, and methods of using those compositions for the treatment of various disease states and conditions, including hyperkinetic disorder, such as drug-induced tardive dyskinesia and Tourette's syndrome.

27 Claims, 12 Drawing Sheets

CRYSTALLINE FORMS OF VALBENAZINE DITOSYLATE

FIELD OF THE INVENTION

The present disclosure relates to crystalline forms of valbenazine ditosylate, processes for preparation thereof, and pharmaceutical compositions of thereof.

BACKGROUND OF THE INVENTION

Valbenazine, also known as NBI-98854, is a highly selective, vesicular monoamine transporter 2 (VMAT2) inhibitor in clinical development for the treatment of tardive dyskinesia. It is a L-valine (2R,3R,11bR)-1,3,4,6,7,11b-hexahydro-9,10-dimethoxy-3-(2-methylpropyl)-2H-benzo(a)quinolizin-2-yl ester and has the following chemical structure according to Formula I.

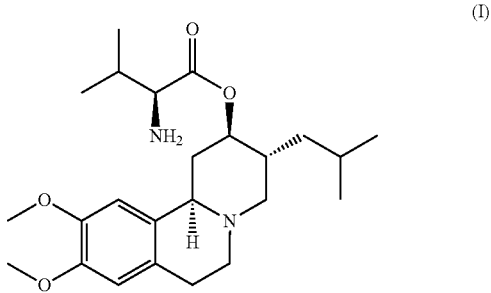

(I)

Valbenazine is an inhibitor of vesicular monoamine transporter isoform 2 (VMAT2) and is being developed for the treatment of different central nervous system disorders, particularly involuntary hyperkinetic movement disorders such as drug-induced tardive dyskinesia and Tourette's syndrome. Valbenazine was approved in the U.S. for the treatment of tardive dyskinesia (TD) and is marketed under the commercial name of INGREZZA® as a ditosylate salt.

U.S. Pat. No. 8,039,627 discloses valbenazine and its pharmaceutically acceptable salts or solvates.

U.S. Pat. No. 10,065,952 discloses six crystalline forms and an amorphous form of valbenazine ditosylate.

Patent application WO 2018/067945 discloses ten crystalline forms of valbenazine ditosylate.

Patent application WO 2019/104141 discloses a crystalline form of valbenazine ditosylate.

Patent application WO 2018/153632 discloses two crystalline forms of valbenazine ditosylate.

Patent applications EP 3,473,623, WO 2018/067945, WO 2018/130345, and WO 2018/153632, disclose crystalline forms of valbenazine and valbenazine salts.

Polymorphism, the occurrence of different crystal forms, is a property of some molecules and molecular complexes. A single compound, like valbenazine, may give rise to a variety of polymorphs having distinct crystal structures and physical properties like melting point, thermal behaviors (e.g., measured by thermogravimetric analysis ("TGA"), differential scanning calorimetry ("DSC") or dynamic vapor sorption ("DVS")), X-ray powder diffraction ("XRPD") pattern, infrared absorption fingerprint and Raman absorption fingerprint. One or more of these techniques may be used to distinguish different polymorphic forms of a compound.

Discovering new solid-state forms, including hydrates and solvates, of an active pharmaceutical ingredient can provide materials having desirable processing properties, such as ease of handling, ease of processing, storage stability, and ease of purification or as desirable intermediate crystal forms that facilitate conversion to other salts or polymorphic forms. New polymorphic forms and solvates of an active pharmaceutical ingredient can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

Hence, there is a need for additional solid-state forms of valbenazine ditosylate with suitable characteristics for an oral formulation.

SUMMARY OF THE INVENTION

The present invention relates to new solid-state crystalline valbenazine ditosylate forms, one designated Form D and the other designated Form E, which are especially suited for use in pharmaceutical compositions for oral administration. Crystalline valbenazine ditosylate Form D can exist in the form of a dichloromethane solvate, while crystalline valbenazine ditosylate Form E can exist in the form of a hydrate.

In another embodiment, the present invention encompasses pharmaceutical compositions comprising crystalline valbenazine ditosylate Form D or Form E, in particular Form D valbenazine ditosylate in the form of a crystalline dichloromethane solvate or Form E crystalline ditosylate in the form of a hydrate; and one or more pharmaceutically acceptable excipient(s).

In another embodiment, the present invention encompasses methods for the treatment, prevention, or amelioration of one or more symptoms of hyperkinetic disorder, and preferably drug-induced tardive dyskinesia and Tourette's syndrome, comprising administering crystalline valbenazine ditosylate Form D or Form E, in particular Form D valbenazine ditosylate in the form of a crystalline dichloromethane solvate or Form E crystalline ditosylate in the form of a hydrate.

In another embodiment, the present invention relates to methods for inhibiting vesicular monoamine transporter isoform 2 in a subject, comprising administering to the subject crystalline valbenazine ditosylate Form D or Form E, in particular Form D valbenazine ditosylate in the form of a crystalline dichloromethane solvate or Form E crystalline ditosylate in the form of a hydrate.

In another embodiment, the present invention relates to crystalline valbenazine ditosylate Form D or Form E, in particular Form D valbenazine ditosylate in the form of a crystalline dichloromethane solvate or Form E crystalline ditosylate in the form of a hydrate, for use as a medicament.

In another embodiment, the present invention relates to crystalline valbenazine ditosylate Form D or Form E, in particular in particular Form D valbenazine ditosylate in the form of a crystalline dichloromethane solvate or Form E crystalline ditosylate in the form of a hydrate, for use in the treatment or prophylaxis of hyperkinetic disorders, and preferably drug-induced tardive dyskinesia and Tourette's syndrome.

In another embodiment, the present invention encompasses process for the preparation of crystalline valbenazine ditosylate Form D, in particular Form D valbenazine ditosylate in the form of a dichloromethane solvate.

In another embodiment, the present disclosure encompasses process for the preparation of crystalline valbenazine ditosylate Form E, in particular Form E valbenazine ditosylate in the form of a crystalline hydrate.

In another embodiment, the present invention relates to a new solid-state form of crystalline valbenazine designated Form F. Crystalline Form F valbenazine ditosylate can exist is the form of a chloroform solvate.

DETAILED DESCRIPTION OF THE INVENTION

The crystalline forms of valbenazine ditosylate according to the present disclosure may have advantageous properties such as at least one of: chemical or polymorphic purity, flowability, solubility, dissolution rate, bioavailability, morphology or crystal habit, stability (such as chemical stability as well as thermal and mechanical stability with respect to polymorphic conversion, stability towards dehydration and/or storage stability), a lower degree of hygroscopicity, low content of residual solvents and advantageous processing and handling characteristics such as compressibility, or bulk density.

A crystalline form may be referred to herein as being characterized by graphical data "as depicted in" a Figure. Such data include, for example, X-ray powder diffractograms and solid-state NMR spectra. As is well-known in the art, the graphical data potentially provides additional technical information to further define the respective solid-state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystalline form of valbenazine ditosylate referred to herein as being characterized by graphical data "as depicted in" a Figure will thus be understood to include any crystal forms of the valbenazine, characterized with the graphical data having such small variations, as are well known to the skilled person, in comparison with the Figure.

The present invention relates to a new crystalline form of valbenazine ditosylate designated Form D, and in particular to Form D crystalline valbenazine ditosylate in the form of a dichloromethane solvate. More specifically, the disclosed crystalline dichloromethane solvate form of valbenazine ditosylate corresponds to a hemi-dichloromethane solvate.

Hence, in one embodiment the present invention relates to crystalline valbenazine ditosylate, designated as Form D, having an X-ray powder diffractogram pattern comprising peaks at 2-theta angles of 6.1, 16.9, 17.2, 19.1 and 19.6±0.2 degrees 2-theta.

In another embodiment, the present invention relates to crystalline valbenazine ditosylate, designated as Form D, having an X-ray powder diffractogram pattern comprising peaks at 2-theta angles of 5.8, 6.1, 10.3, 16.9, 17.2, 17.6, 19.1, 19.6, 20.7 and 22.5±0.2 degrees 2-theta.

Figure 1:
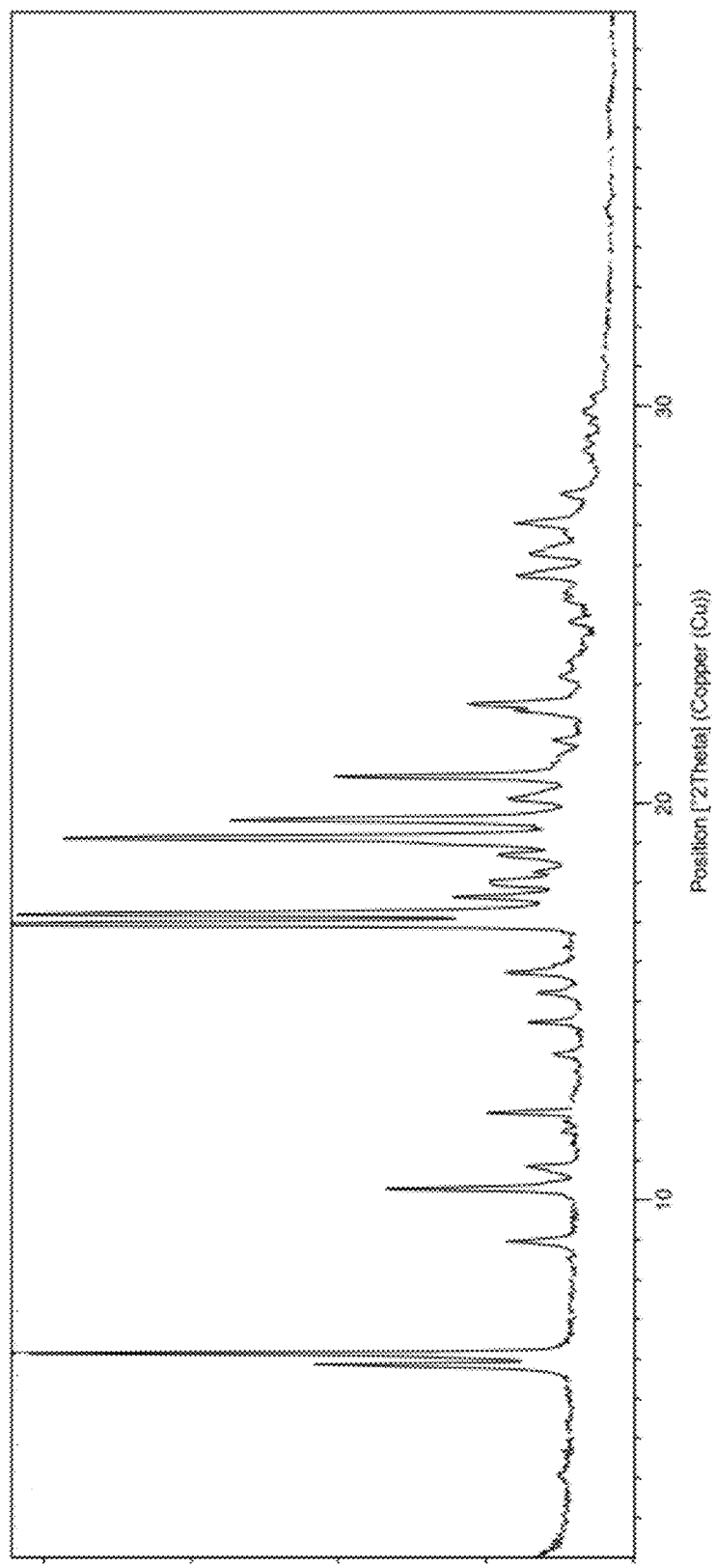
FIG. 1 shows an X-ray powder diffractogram (XRPD) pattern of Form D of valbenazine ditosylate.

In another embodiment, the present invention relates to crystalline valbenazine ditosylate, designated as Form D, having an X-ray powder diffractogram pattern essentially the same as shown in FIG. 1.

Figure 2:
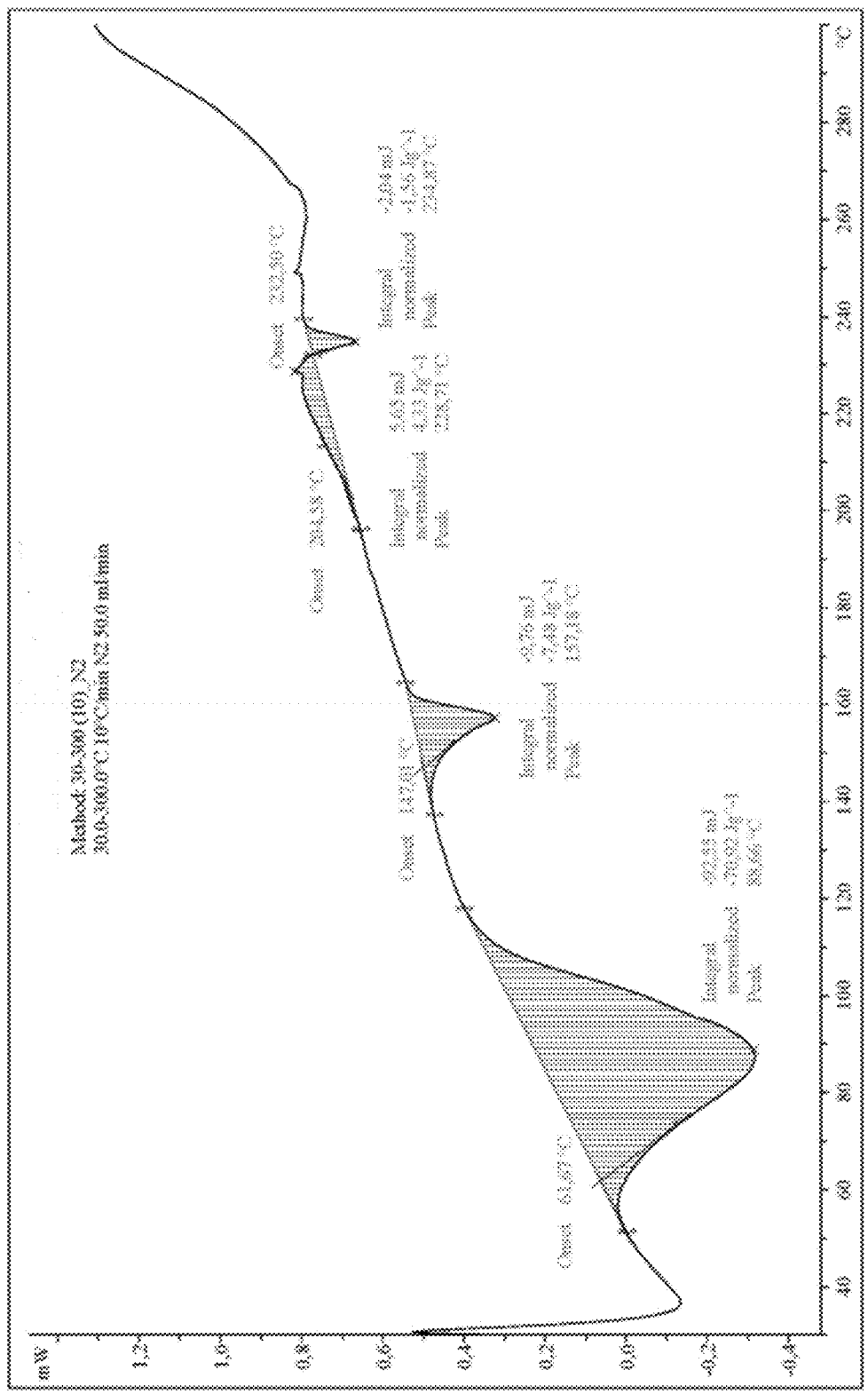
FIG. 2 shows a DSC of Form D of valbenazine ditosylate.
Figure 3:
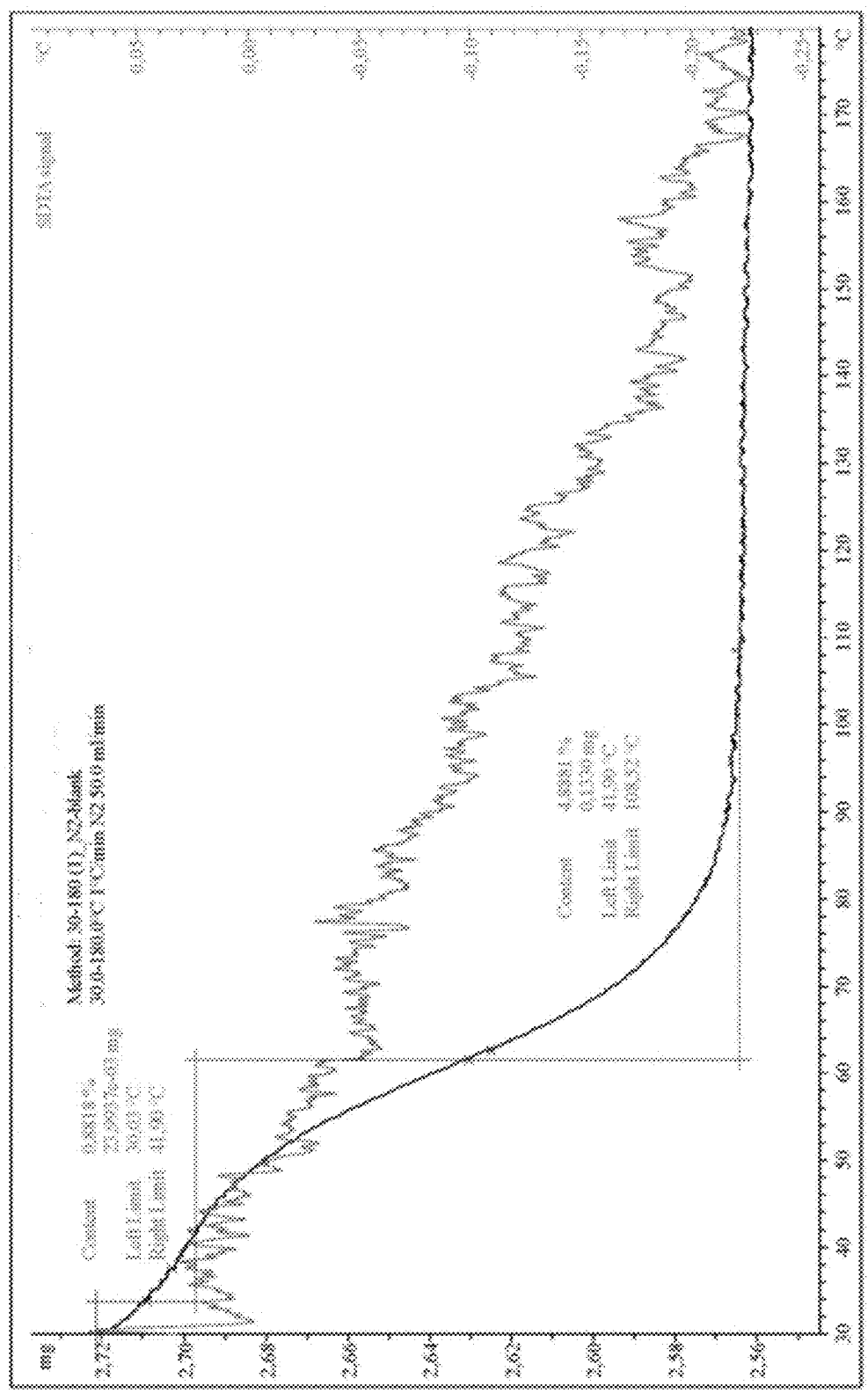
FIG. 3 shows a TGA of Form D of valbenazine ditosylate.
Figure 4:
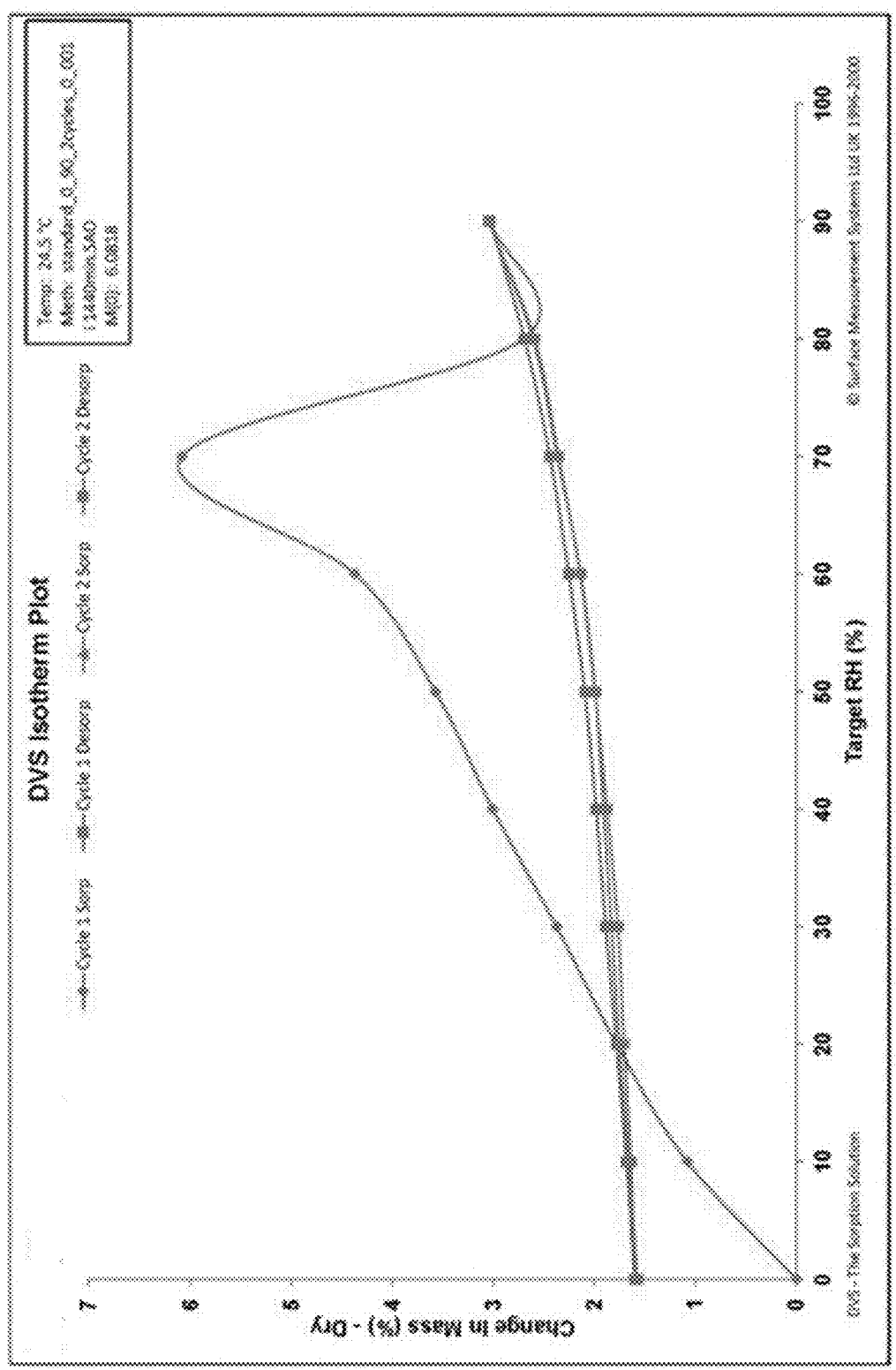
FIG. 4 shows a DVS of Form D of valbenazine ditosylate.

In another embodiment, the present invention relates to crystalline valbenazine, designated as Form D, having at least one of the following:
a) a differential scanning calorimetry curve essentially the same as shown in FIG. 2, when measured at a heating rate of 10° C./min;
b) a TGA essentially the same as shown in FIG. 3, when measured at a rate of 1° C./min; or
c) a DVS essentially the same as shown in FIG. 4, when measured with a method using two cycles (0% to 90% RH) and (90% to 0% RH).

In certain embodiments, the present invention relates to crystalline valbenazine ditosylate, designated as Form D, having an X-ray powder diffractogram pattern essentially the same as shown in FIG. 1 and whose cell indexation has the following parameters: a=30.146(9)Å, b=14.389(9)Å, c=10.449(3)Å, α=β=γ=90.0°, and volume=4532(3)Å3.

In a different embodiment, the present invention relates to a new crystalline form of valbenazine ditosylate designated Form E, and in particular to a Form E valbenazine ditosylate hydrate. More specifically, the disclosed Form E crystalline valbenazine ditosylate hydrate corresponds to a monohydrate.

In another embodiment, the present invention relates to crystalline valbenazine ditosylate, designated as Form E, having an X-ray powder diffractogram pattern comprising peaks at 2-theta angles of 5.8, 6.8, 15.9, 17.0 and 18.6±0.2 degrees 2-theta.

In another embodiment, the present invention relates to a crystalline valbenazine ditosylate, designated as Form E, having an X-ray powder diffractogram pattern comprising peaks at 2-theta angles of 5.8, 6.8, 13.7, 15.4, 15.9, 17.0, 18.0, 18.6, 19.9 and 22.6±0.2 degrees 2-theta.

Figure 5:
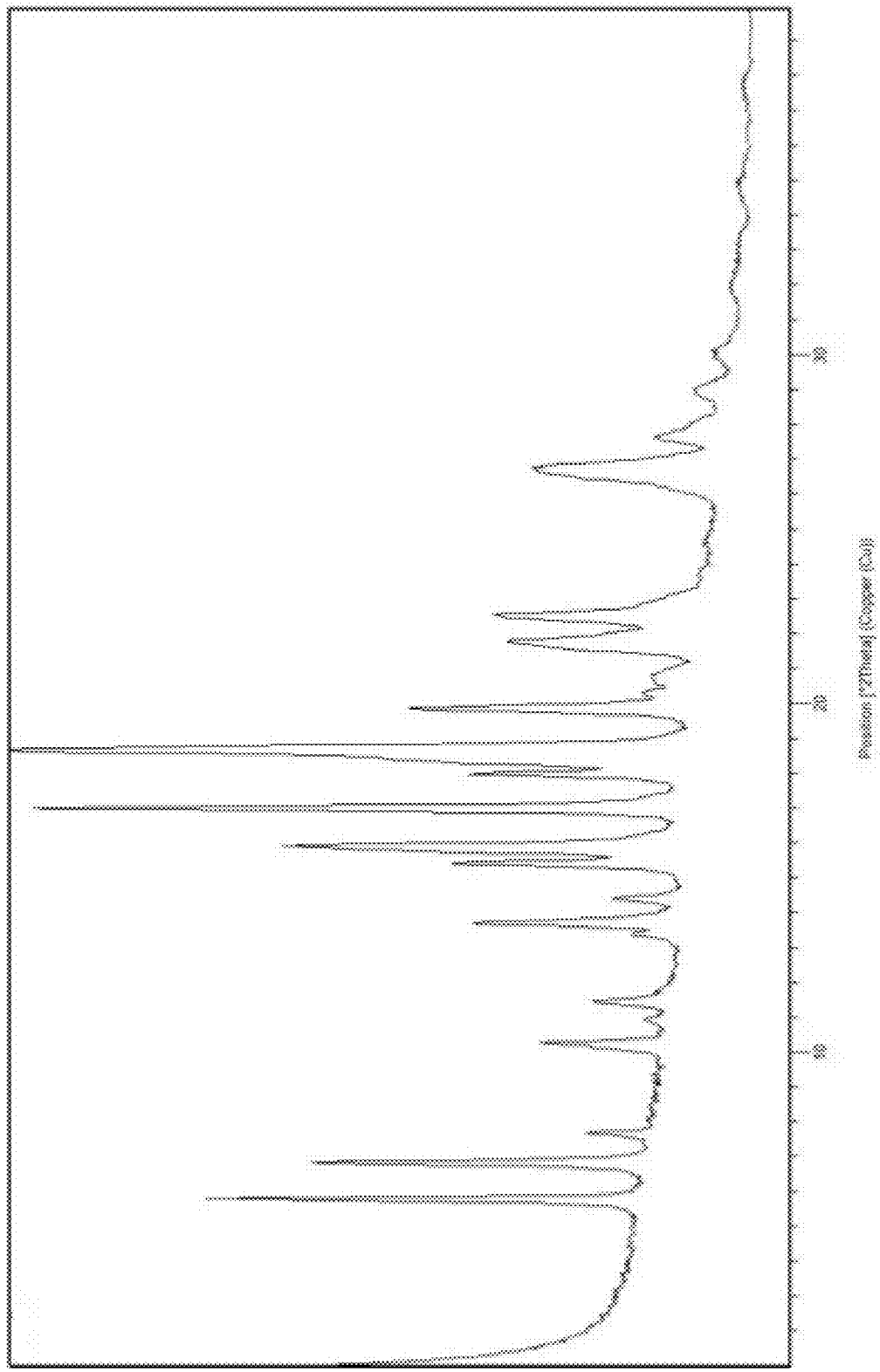
FIG. 5 shows an X-ray powder diffractogram (XRPD) pattern of Form E of valbenazine ditosylate.

In another embodiment, the present invention relates to a crystalline valbenazine ditosylate, designated as Form E, having an X-ray powder diffractogram pattern essentially the same as shown in FIG. 5.

Figure 6:
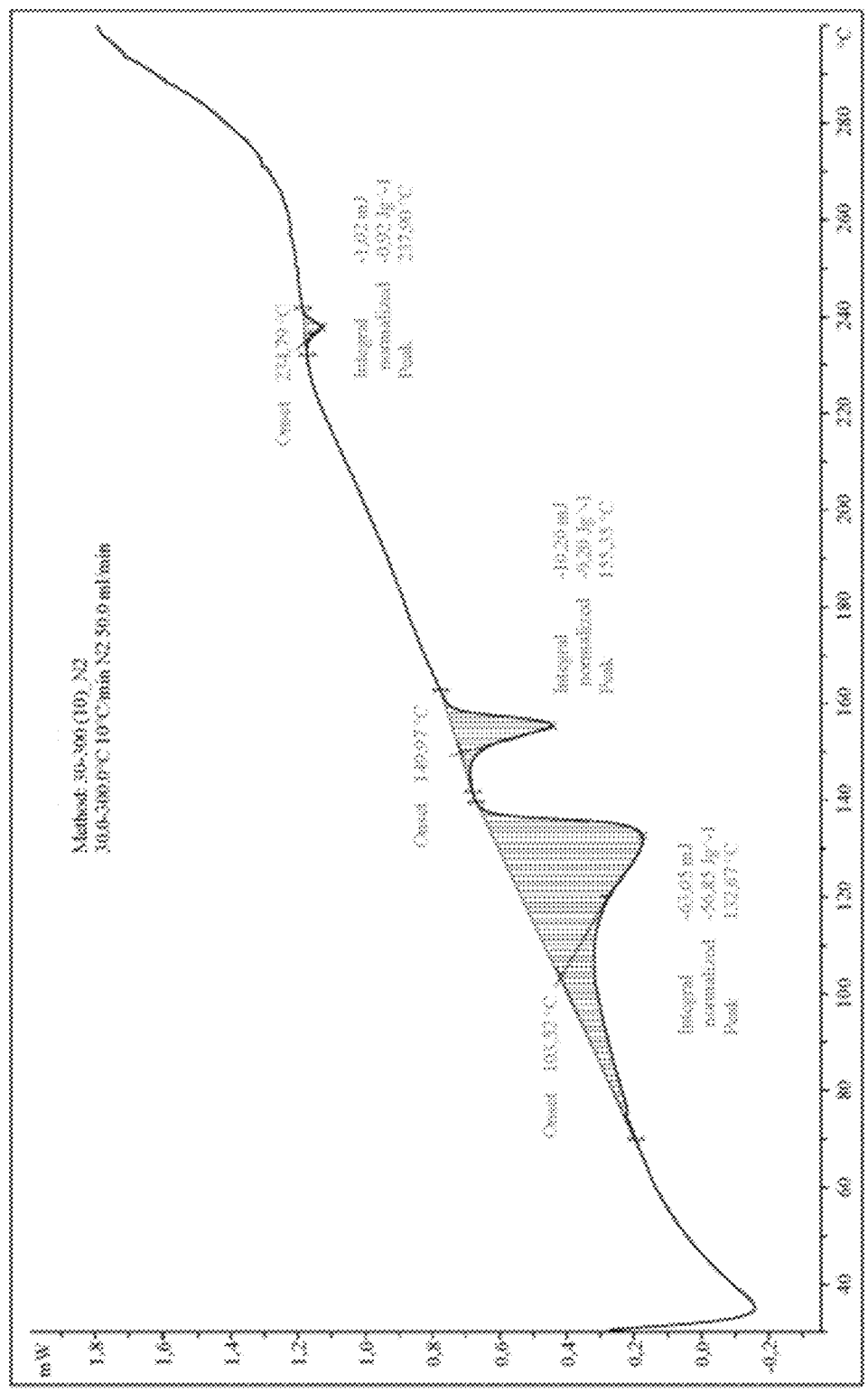
FIG. 6 shows a DSC of Form E of valbenazine ditosylate.
Figure 7:
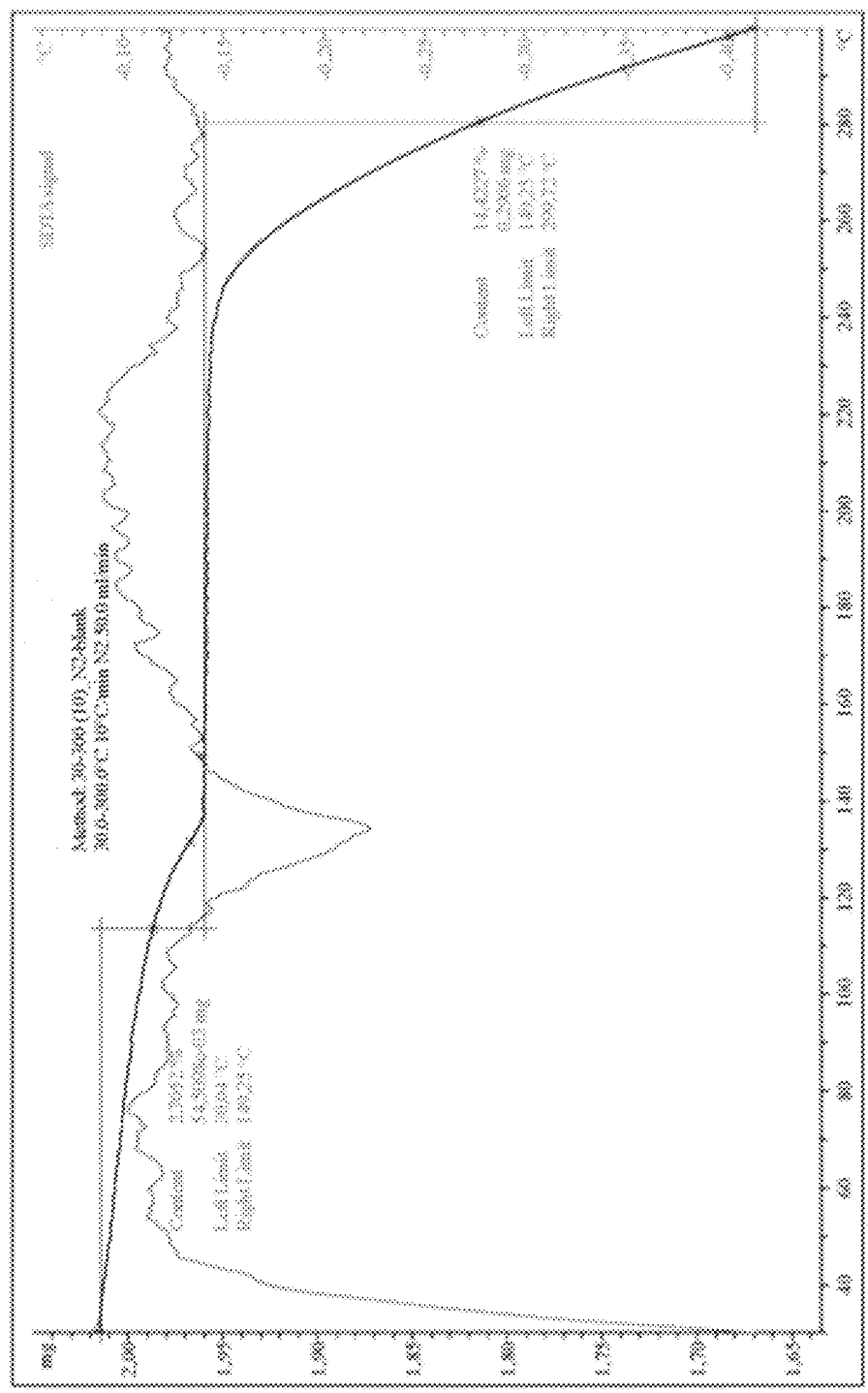
FIG. 7 shows a TGA of Form E of valbenazine ditosylate.
Figure 8:
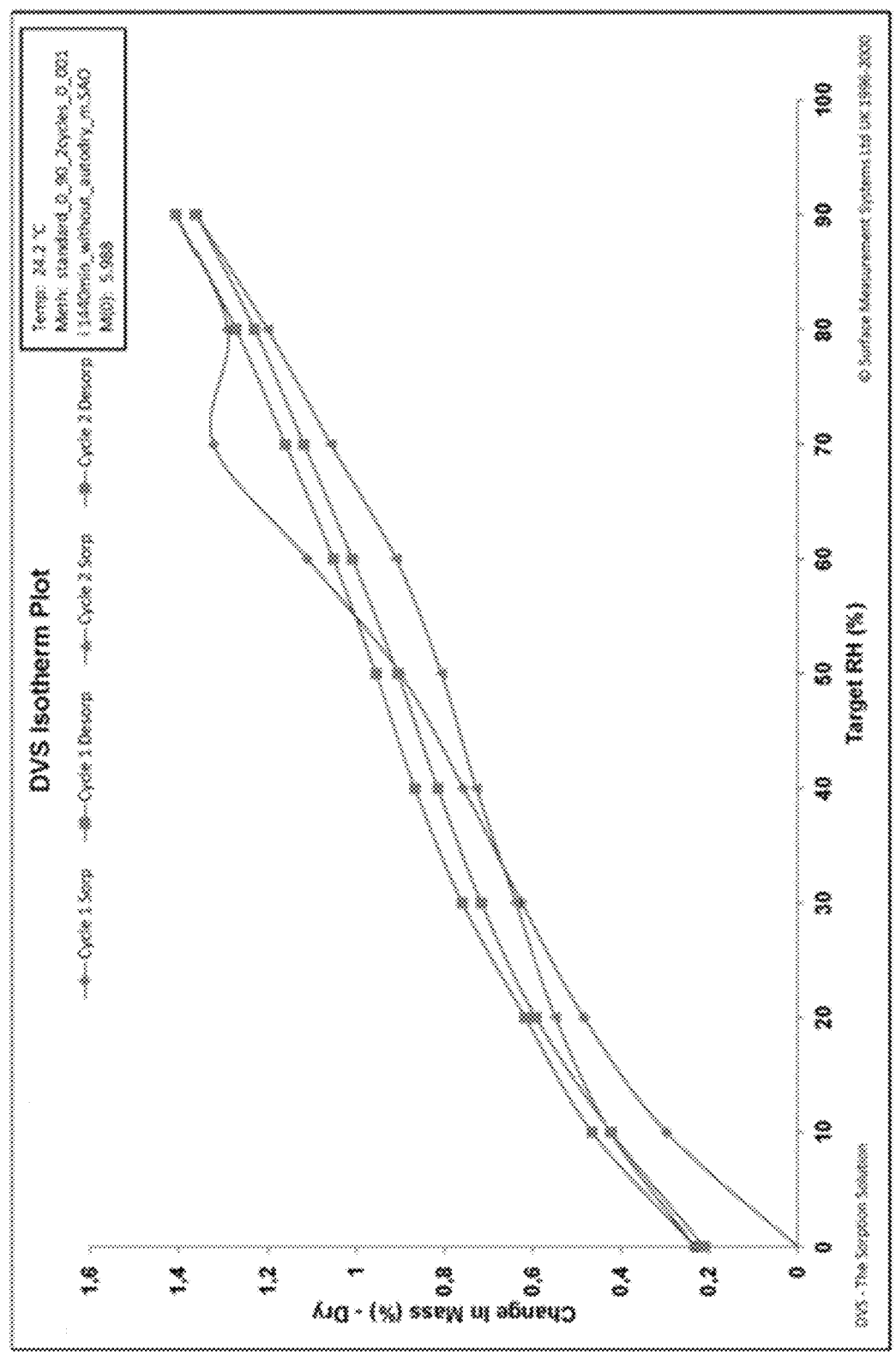
FIG. 8 shows a DVS of Form E of valbenazine ditosylate.

In another embodiment, the present invention relates to crystalline valbenazine ditosylate, designated as Form E, having at least one of the following:

a) a differential scanning calorimetry curve essentially the same as FIG. 6, when measured at a heating rate of 10° C./min;
b) a TGA essentially the same as shown in FIG. 7 of the present invention, when measured at a rate of 10° C./min; or
c) a DVS essentially the same as shown in FIG. 8 of the present invention, when measured with a method using two cycles (0% to 90% RH) and (90% to 0% RH).

In certain embodiments, the present invention relates to crystalline valbenazine ditosylate, designated as Form E, having an X-ray powder diffractogram pattern essentially the same as shown in FIG. 5 and whose cell indexation is compatible with a triclinic cell, with the following parameters: a=18.944(7) Å, b=13.400(3) Å, c=10.422(2) Å, α=89.38(2), β=23.44(2), γ=03.36(2°) and volume=2126 (1) Å 3.

In a different embodiment, the present disclosure relates to pharmaceutical compositions comprising crystalline valbenazine ditosylate, designated as Form D, and one or more pharmaceutically acceptable excipient(s). More specifically, the present disclosure relates the present disclosure relates to a pharmaceutical composition as an oral solid dosage form comprising crystalline valbenazine ditosylate, designated as Form D, and one or more pharmaceutically acceptable excipient(s).

In a different embodiment, the present disclosure relates to pharmaceutical compositions comprising crystalline valbenazine ditosylate, designated as Form E, and one or more pharmaceutically acceptable excipient(s). More specifically, the present disclosure relates to a pharmaceutical composition as an oral solid dosage form comprising crystalline valbenazine ditosylate, designated as Form E, and one or more pharmaceutically acceptable excipient(s).

In a different embodiment, the present disclosure relates to pharmaceutical composition comprising crystalline valbenazine ditosylate, designated as Form D, or crystalline valbenazine ditosylate, designated as Form E, and one or more pharmaceutically acceptable excipient(s). More specifically, the present disclosure relates to a pharmaceutical composition as an oral solid dosage form comprising crystalline valbenazine ditosylate, designated as Form D, or crystalline valbenazine ditosylate, designated as Form E, and one or more pharmaceutically acceptable excipient(s).

In this regard, the DSC and DVS data provided in FIG. 2 and FIG. 4 respectively, indicate that the valbenazine ditosylate designated as Form D of the present invention is stable against temperature stress in an acceptable margins for being formulated into an oral solid dosage form, i.e. by dry granulation, where significant temperature stress is generated during manufacture.

The DSC and DVS data provided in FIG. 6 and FIG. 8, respectively, indicate that crystalline valbenazine ditosylate designated as Form E of the present invention is stable against temperature stress in an acceptable margins for being formulated into an oral solid dosage form, i.e. by dry granulation or wet granulation, where significant temperature stress is generated during manufacture.

With respect to the pharmaceutical compositions of the invention, the crystalline valbenazine ditosylate Forms D and E of the invention can be present in amounts including but not limited to amounts equivalent to 40 mg of valbenazine free base or 80 mg valbenazine free base.

In a different embodiment, the present disclosure relates to a method for the treatment, prevention, or amelioration of one or more symptoms of hyperkinetic disorder, and preferably drug-induced tardive dyskinesia and Tourette's syndrome, comprising administering crystalline valbenazine ditosylate, designated as Form D.

In a different embodiment, the present disclosure relates to a method for the treatment, prevention, or amelioration of one or more symptoms of hyperkinetic disorder, and preferably drug-induced tardive dyskinesia and Tourette's syndrome, comprising administering pharmaceutical composition comprising crystalline valbenazine ditosylate, designated as Form D, and one or more pharmaceutically acceptable excipient(s). More specifically, the present disclosure relates the present disclosure relates to a method for the treatment, prevention, or amelioration of one or more symptoms of hyperkinetic disorder, and preferably drug-induced tardive dyskinesia and Tourette's syndrome, comprising administering pharmaceutical composition as an oral solid dosage form comprising crystalline valbenazine ditosylate, designated as Form D, and one or more pharmaceutically acceptable excipient(s).

In a different embodiment, the present disclosure relates to a method for the treatment, prevention, or amelioration of one or more symptoms of hyperkinetic disorder, and preferably drug-induced tardive dyskinesia and Tourette's syndrome, comprising administering crystalline valbenazine ditosylate, designated as Form E.

In a different embodiment, the present disclosure relates to a method for the treatment, prevention, or amelioration of one or more symptoms of hyperkinetic disorder, and preferably drug-induced tardive dyskinesia and Tourette's syndrome, comprising administering pharmaceutical composition comprising crystalline valbenazine ditosylate, designated as Form E, and one or more pharmaceutically acceptable excipient(s). More specifically, the present disclosure relates the present disclosure relates to a method for the treatment, prevention, or amelioration of one or more symptoms of hyperkinetic disorder, and preferably drug-induced tardive dyskinesia and Tourette's syndrome, comprising administering pharmaceutical composition as an oral solid dosage form comprising crystalline valbenazine ditosylate, designated as Form E, and one or more pharmaceutically acceptable excipient(s).

In a different embodiment, the present disclosure relates to a method for the treatment, prevention, or amelioration of one or more symptoms of hyperkinetic disorder, and preferably drug-induced tardive dyskinesia and Tourette's syndrome, comprising administering crystalline valbenazine ditosylate, designated as Form D, or crystalline valbenazine, designated as Form E.

In a different embodiment, the present disclosure relates to a method for the treatment, prevention, or amelioration of one or more symptoms of hyperkinetic disorder, and preferably drug-induced tardive dyskinesia and Tourette's syndrome, comprising administering pharmaceutical composition comprising crystalline valbenazine ditosylate, designated as Form D, or crystalline valbenazine ditosylate, designated as Form E, and one or more pharmaceutically acceptable excipient(s). More specifically, the present disclosure relates the present disclosure relates to a method for the treatment, prevention, or amelioration of one or more symptoms of hyperkinetic disorder, and preferably drug-induced tardive dyskinesia and Tourette's syndrome, comprising administering pharmaceutical composition as an oral solid dosage form comprising crystalline valbenazine ditosylate dichloromethane, designated as Form D, or crystalline valbenazine ditosylate, designated as Form E, and one or more pharmaceutically acceptable excipient(s).

In a different embodiment, the present disclosure relates to a method for inhibiting vesicular monoamine transporter isoform 2 in a subject comprising administering crystalline valbenazine ditosylate, designated as Form D.

In a different embodiment, the present disclosure relates to a method for inhibiting vesicular monoamine transporter isoform 2 in a subject comprising administering pharmaceutical composition comprising crystalline valbenazine ditosylate, designated as Form D, and one or more pharmaceutically acceptable excipient(s). More specifically, the present disclosure relates the present disclosure relates to a method for inhibiting vesicular monoamine transporter isoform 2 in a subject comprising administering pharmaceutical composition as an oral solid dosage form comprising crystalline valbenazine ditosylate, designated as Form D, and one or more pharmaceutically acceptable excipient(s).

In a different embodiment, the present disclosure relates to a method for inhibiting vesicular monoamine transporter isoform 2 in a subject comprising administering crystalline valbenazine ditosylate, designated as Form E.

In a different embodiment, the present disclosure relates to a method for inhibiting vesicular monoamine transporter isoform 2 in a subject comprising administering pharmaceutical composition comprising crystalline valbenazine ditosylate, designated as Form E, and one or more pharmaceutically acceptable excipient(s). More specifically, the present disclosure relates the present disclosure relates to a method for inhibiting vesicular monoamine transporter isoform 2 in a subject comprising administering pharmaceutical composition as an oral solid dosage form comprising crystalline valbenazine ditosylate, designated as Form E, and one or more pharmaceutically acceptable excipient(s).

In a different embodiment, the present disclosure relates to a method for inhibiting vesicular monoamine transporter isoform 2 in a subject comprising administering pharmaceutical composition comprising crystalline valbenazine ditosylate, designated as Form D, or crystalline valbenazine ditosylate, designated as Form E, and one or more pharmaceutically acceptable excipient(s). More specifically, the present disclosure relates the present disclosure relates to a method for inhibiting vesicular monoamine transporter isoform 2 in a subject comprising administering pharmaceutical composition as an oral solid dosage form comprising crystalline valbenazine ditosylate, designated as Form D, or crystalline valbenazine, designated as Form E, and one or more pharmaceutically acceptable excipient(s).

In the above-noted methods, the crystalline valbenazine ditosylate Forms D and E of the invention can be administered in amounts equivalent to 40 mg of valbenazine free base or 80 mg valbenazine free base per day.

In a different embodiment, the present invention relates to a crystalline valbenazine ditosylate, designated as Form D, for use a medicament.

In a different embodiment, the present invention relates to a crystalline valbenazine ditosylate, designated as Form E, for use a medicament.

In a different embodiment, the present invention relates to a crystalline valbenazine ditosylate, designated as Form D, for use in the treatment or prophylaxis of hyperkinetic disorders, and preferably drug-induced tardive dyskinesia and Tourette's syndrome.

In a different embodiment, the present invention relates to a crystalline valbenazine ditosylate, designated as Form E, for use in the treatment or prophylaxis of hyperkinetic disorders, and preferably drug-induced tardive dyskinesia and Tourette's syndrome.

In a different embodiment, the present disclosure relates to a process for the preparation of crystalline valbenazine ditosylate, designated as Form D, comprising:

(i) reacting valbenazine with p-toluenesulfonic acid monohydrate in dichloromethane at room temperature;
(ii) slurrying the reaction mixture of step
(iii) filtering the organic layer from the slurry at room temperature;
(iv) obtaining a solid product; and
(iv) drying the solid product under vacuum.

In a different embodiment, the present disclosure relates to a process for the preparation of crystalline valbenazine ditosylate, designated as Form E, comprising:

(i) reacting valbenazine with p-toluenesulfonic acid monohydrate in chloroform at a temperature from about 45° C. to about 60° C.;
(ii) slurrying the reaction mixture of step (i);
(iii) filtering the organic layer from the slurry at room temperature;
(iv) obtaining a solid product; and
(iv) drying the solid product under vacuum.

Figure 9:
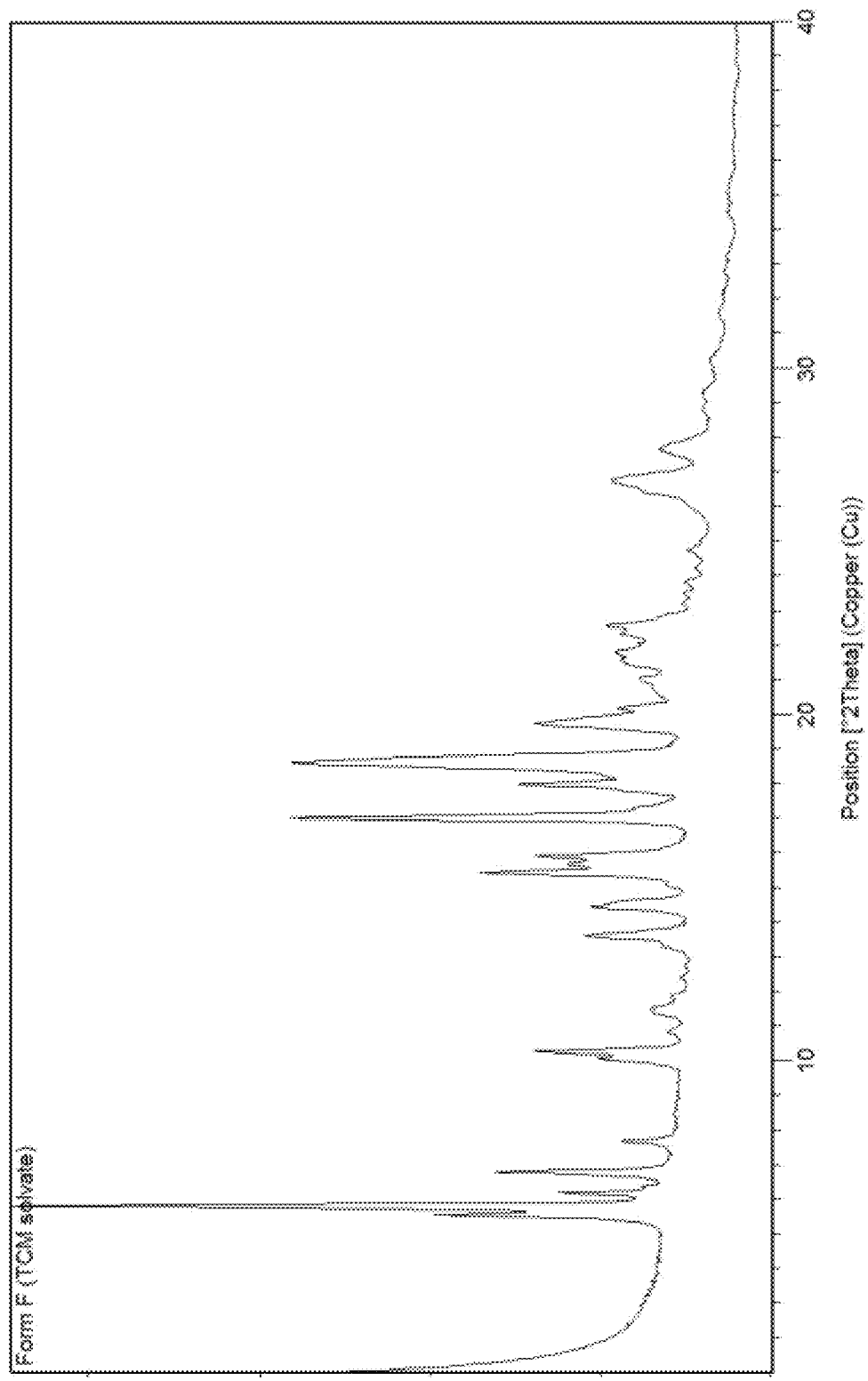
FIG. 9 shows an X-ray powder diffractogram (XRPD) pattern of Form F of valbenazine ditosylate.

In a further embodiment, a new solid-state form of crystalline valbenazine, designated Form F, has been found. Specifically, Crystalline Form F valbenazine ditosylate in the form of a chloroform solvate has been formed and isolated during preparation of crystalline Form E valbenazine ditosylate. Without being bound by theory, Form F valbenazine ditosylate is believed to be thermodynamically and kinetically disfavored over Form E valbenazine ditosylate in solution under certain reaction conditions. Crystalline Form F valbenazine ditosylate has an X-ray powder diffractogram pattern essentially the same as shown in FIG. 9. More specifically, the crystalline Form F valbenazine ditosylate has an X-ray powder diffractogram pattern comprising peaks at 2-theta angles of 5.5, 5.8, 6.8, 10.3, 15.4, 15.9, 17.0, 18.0, 18.6 and 19.7±0.2 degrees 2-theta.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

DESCRIPTIONS

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture.

As used herein, the term "under vacuum" refers to drying process carried out at a pressure of about 10 mbar to about 50 mbar.

As used herein, the term "slow cooling" means a cooling process wherein the cooling temperature of a media was performed at a rate of less than 1° C. per minute.

As used herein, the term "room temperature" means a temperature between 20° C. and 25° C.

Analytical Methods Definitions

As used herein, XRPD means X-Ray Powder Diffraction Analysis. Unless stated otherwise, XRPDs were performed at 20-30° C. using Cu Kα radiation, 1=1.5418 Å. X-ray powder diffraction analysis were performed according to the following equipment and conditions: PANalytical X'Pert PRO MPD 2 Theta powder diffractometer of 240 millimetres of radius, in a configuration of convergent beam with a focalizing mirror and a transmission geometry with flat samples sandwiched between low absorbing films. Cu Kα radiation ($\lambda$=1.5418 Å). Work power: 45 kV-40 mA. Incident beam slits defining a beam height of 0.4 millimetres. Incident and diffracted beam 0.02 radians Soller slits. PIXcel detector: Active length=3.347°. 2 Theta scans from 1 to 40° 2θ with a step size of 0.026° 2 Theta and a measuring time of 298 seconds per step. The powder samples were sandwiched between films of polyester of 3.6 microns of thickness. Silicon powder was used as an internal standard for calibration.

As used herein, TGA means Thermogravimetric Analysis. Unless stated otherwise, TGAs were performed according to the following equipment and conditions: Mettler Toledo Thermobalance TGA/SDTA851e. Crucible: Alumina crucible with a capacity of 70 μL. Gas: Dry nitrogen 50 mL/min. Method standard: Heating from 30° C. to 300° C. at a rate of 1-10° C./min. A blank curve has been previously performed by using the same methodology and it has been subtracted.

As used herein, DVS means Dynamic Vapour Sorption Analysis. Unless stated otherwise, DVSs were performed according to the following equipment and conditions: DVS-1000 instrument by Surface Measurement Systems was used. Samples were prepared by transferring them into an aluminum crucible and loading this into the DVS. A method utilizing two cycles (0% to 90% RH) and (90% to 0% RH) was run. The equilibrium condition for each step was set to a mass constancy of ±0.001% over 60 min and a maximum time limit of 1440 min for each step. This method was undertaken at 25° C.

As used herein, DSC means Differential Scanning calorimetry Analysis. Unless stated otherwise, DSCs were performed according to the following equipment and conditions: DSC 822e Mettler Toledo. Crucible: Aluminum crucible with a capacity of 40 μL and with hole the lid. Gas: Dry nitrogen 50 mL/min. Method standard: Heating from 30° C. to 300° C. at a rate of 10° C./min.

As used herein, $H^1$ NMR means Proton Nuclear magnetic resonance spectroscopy Analysis. Unless stated otherwise, H-RMNs were performed according to the following conditions: DMSO-d 6/delay: 1/pulse: 45°/scans: 32.

EXAMPLES

Valbenazine starting material can be prepared according to methods within the purview of the skilled artisan. For example, the methods disclosed in U.S. Pat. No. 8,039,627 can be used.

Example 1

Synthesis of Valbenazine
(R,R,R)-1,3,4,6,7,11b-Hexahydro-9,10-dimethoxy-3-(2-methylpropyl)-2H-benzo[a]quinolizin-2-ol (Compound 1; 10.3 grams, 0.032 mol, 1 eq), carbobenzyloxy-L-valine (Z-Val-OH; 13.0 grams, 0.052 mol, 1.6 eq), 4-(dimethyamino)pyridine (DMAP; 0.4 grams, 0.003 mol, 0.1 eq) were dissolved in dichloromethane (100 ml, 10 vol) at room temperature. Then N-(3-dimethylaminopropyl)-N'-ethylcarbodiimide hydrochloride (EDC.HCl; 9.9 grams, 0.052 mol, 1.6 eq) was added and the reaction mixture was stirred at room temperature for 3 hours. Upon completion, the reaction mixture was washed with NaHCO$_3$, then with aqueous HCl and at last with water. The organic layer was concentrated, and methanol was added (100 ml, 10 vol). Then Pd/C was added, and the mixture was purged with hydrogen gas. The mixture was stirred for 2 hours, filtered through celite and the valbenazine obtained was maintained as methanolic dissolution.

Example 2

Preparation of Form D Valbenazine Ditosylate.

A valbenazine methanolic solution obtained according to preparative example 1 was concentrated. Dichloromethane (100 ml, 10 vol) was added at room temperature. p-toluene-sulfonic acid (11.9 grams, 0.064 mol, 2 eq) in water (10 ml, 1 vol) were added and the mixture was stirred for ½ hour. After settling, the water layer was discharged and the organic layer was washed with water (20 ml, 2 vol). Then, the organic layer was concentrated under vacuum to obtain a solid product (20.4 grams, 0.027 mol, 83% yield, 99.85% purity). 2 g of the obtained product was dried under vacuum oven at 40° C. for 120 hours to obtain crystalline valbenazine ditosylate. The crystalline valbenazine ditosylate was then characterized by XRPD as Form D, having a XRPD pattern as depicted in FIG. 1 with the following peaks, expressed in degrees 2-theta:

| Pos. [°2Th.] | FWHM [°2Th.] | Rel. Int. [%] |
| --- | --- | --- |
| 3.0524 | 0.2047 | 1.42 |
| 5.8396 | 0.0768 | 37.34 |
| 6.1303 | 0.0768 | 85.98 |
| 8.9451 | 0.1023 | 9.91 |
| 10.2817 | 0.0768 | 28.27 |
| 10.8395 | 0.1023 | 7.19 |
| 11.7365 | 0.0768 | 1.57 |
| 12.1996 | 0.0768 | 13.00 |
| 13.6606 | 0.1023 | 3.73 |
| 14.4716 | 0.0768 | 7.67 |
| 15.2188 | 0.1023 | 5.69 |
| 15.7258 | 0.1023 | 9.97 |
| 16.9454 | 0.1023 | 100.00 |
| 17.1989 | 0.1023 | 82.49 |
| 17.6412 | 0.1023 | 15.83 |
| 17.9393 | 0.1279 | 10.03 |
| 18.2733 | 0.0768 | 3.58 |
| 18.6845 | 0.1023 | 9.27 |
| 19.1245 | 0.1023 | 74.01 |
| 19.5844 | 0.1023 | 48.31 |
| 20.0932 | 0.1023 | 7.85 |
| 20.6610 | 0.1023 | 34.07 |
| 21.5787 | 0.1791 | 3.46 |
| 22.3028 | 0.0768 | 8.90 |
| 22.4941 | 0.1279 | 16.30 |
| 23.1862 | 0.1535 | 3.22 |
| 23.5885 | 0.1535 | 2.07 |
| 24.1074 | 0.1535 | 0.73 |
| 24.5508 | 0.1535 | 2.66 |
| 25.1122 | 0.0768 | 2.82 |
| 25.7131 | 0.1279 | 9.52 |
| 26.2586 | 0.1023 | 7.36 |
| 27.0543 | 0.1279 | 9.47 |
| 27.7906 | 0.1535 | 4.66 |
| 28.8600 | 0.1535 | 2.07 |

-continued

| Pos. [°2Th.] | FWHM [°2Th.] | Rel. Int. [%] |
|---|---|---|
| 29.1501 | 0.1535 | 1.61 |
| 29.3450 | 0.1791 | 2.53 |
| 30.2652 | 0.1023 | 1.86 |
| 34.9274 | 0.2047 | 0.84 |

The XRPD pattern was indexed by the LeBail method and the parameters are as follows: a=30.146(9)Å, b=14.389(9)Å, c=10.449(3)Å, α=β=γ=90.0°, and volume=4532(3)Å3.

This crystalline form of valbenazine ditosylate was also subjected to DSC, TGA, and DVS. The DSC analysis, as shown in FIG. 2, shows a first endothermic phenomenon at 62° C. with an associated heat of 70.9 J/g, a second endothermic phenomenon at 147° C. with an associated heat of 7.5 J/g, an exothermic phenomenon at 204.6° C. with an associated heat of 4.3 J/g and finally a third endothermic phenomenon at 233° C. with an associated heat of 1.6 J/g and a weight loss of 4.9% from 42° C. to 109° C. observed in a TGA analysis, as shown in FIG. 3.

DVS analysis at 25° C. in the first cycle shows water sorption by the sample up to approximately 6.0% at 70% relative humidity, then it shows water desorption by the sample up to 4.0% at 80% relative humidity, as shown in FIG. 4. It is believed based on XRPD analysis that this phenomenon is associated with transformation to polymorphic form II, as disclosed, for example in U.S. Pat. No. 10,065,952.

Figure 10:
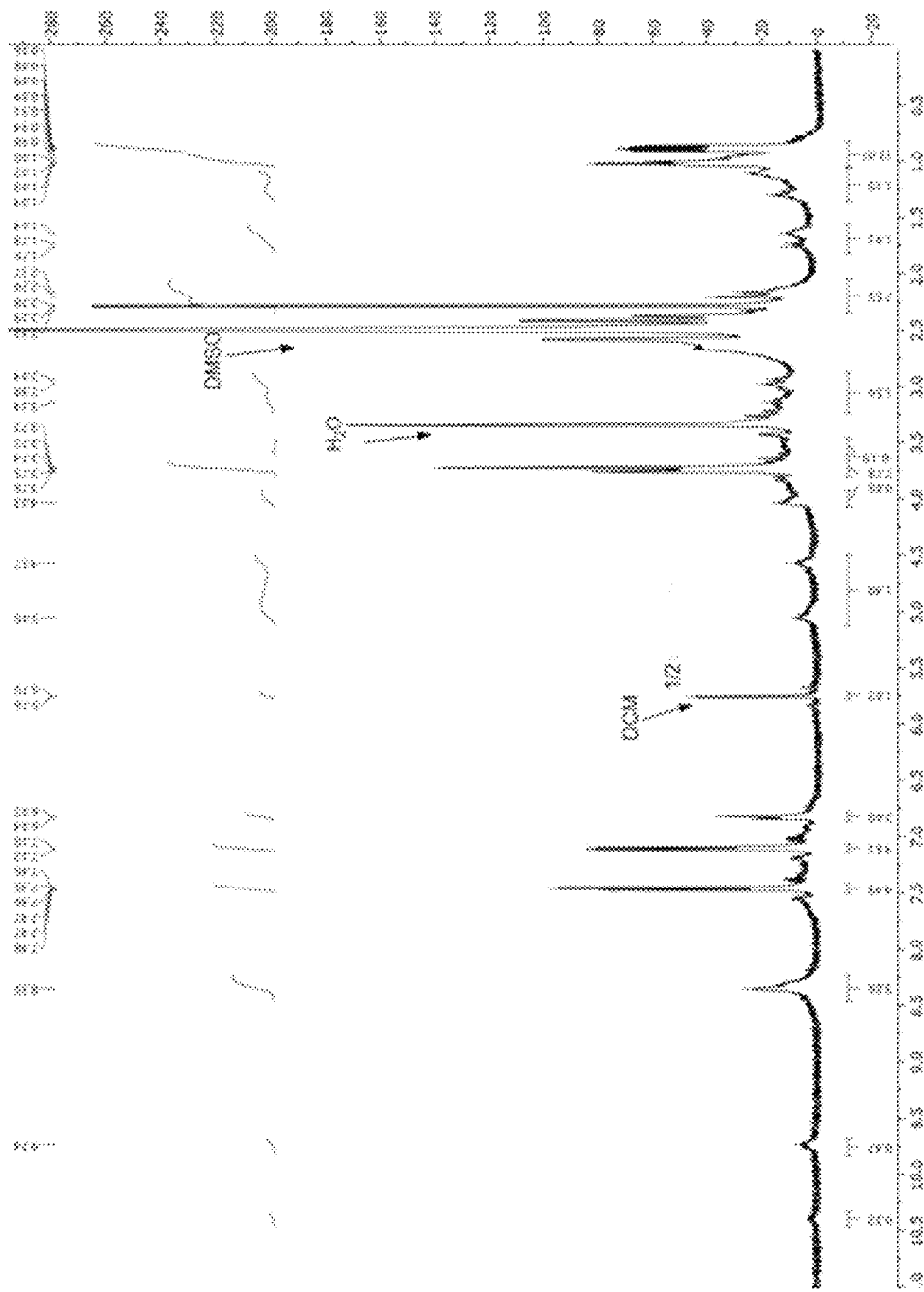
FIG. 10 shows a $H^1$ NMR spectrum of Form D of valbenazine ditosylate.

The crystalline valbenazine ditosylate of this example was also analyzed by NMR. The results, shown in FIG. 10, confirm it to be a dichlormethane solvate of valbenazine ditosylate.

Example 3

Preparation of Form E Valbenazine Ditosylate.

A valbenazine methanolic solution obtained according to preparative example 1 was concentrated. Chloroform (120 ml, 12 vol) was added at room temperature. p-toluenesulfonic acid (11.9 grams, 0.064 mol, 2 eq) and water (10 ml, 1 vol) were added and the mixture was heated to reflux until complete dissolution. After that, the mixture was slow cooled to room temperature and stirred for 14 hours, then filtered and washed with chloroform (3*20 ml, 3*2 vol). The product was dried under vacuum at 60° C. for 48 hours to obtain crystalline valbenazine ditosylate. (18.7 grams, 0.025 mol, 76% yield, 99.94% purity). The crystalline valbenazine ditosylate was then characterized by XRPD as Form E, having a XRPD pattern as depicted in FIG. 5 with the following peaks, expressed in degrees 2-theta:

| Pos. [°2Th.] | d-spacing [Å] | Rel. Int. [%] |
|---|---|---|
| 5.7955 | 15.24985 | 64.85 |
| 6.8303 | 12.94166 | 50.31 |
| 7.6759 | 11.51767 | 9.59 |
| 10.2742 | 8.61006 | 18.00 |
| 10.9497 | 8.08035 | 2.73 |
| 11.4684 | 7.71606 | 10.94 |
| 13.3621 | 6.67647 | 6.51 |
| 13.6922 | 6.46743 | 30.34 |
| 14.4034 | 6.14966 | 9.93 |
| 15.4034 | 5.75261 | 33.38 |
| 15.7642 | 5.62174 | 40.02 |
| 15.9237 | 5.56577 | 56.96 |
| 16.9924 | 5.21806 | 96.98 |
| 17.9695 | 4.93645 | 30.82 |
| 18.2748 | 4.85469 | 30.40 |
| 18.6398 | 4.76045 | 100.00 |
| 19.8527 | 4.47225 | 40.71 |
| 20.3401 | 4.36618 | 4.78 |
| 20.8106 | 4.26851 | 4.14 |
| 21.5350 | 4.12654 | 16.12 |
| 21.7869 | 4.07940 | 26.18 |
| 22.5618 | 3.94102 | 27.85 |
| 23.7714 | 3.74313 | 0.42 |
| 24.6673 | 3.60918 | 0.71 |
| 26.4565 | 3.36903 | 19.13 |
| 26.8462 | 3.32100 | 22.94 |
| 27.5289 | 3.24018 | 6.73 |
| 27.8566 | 3.20279 | 5.10 |
| 29.0457 | 3.07432 | 4.00 |
| 30.1641 | 2.96284 | 2.41 |
| 31.9052 | 2.80502 | 0.85 |
| 33.3872 | 2.68382 | 0.60 |
| 34.8759 | 2.57260 | 0.98 |
| 37.8192 | 2.37888 | 0.98 |

The XRPD pattern was indexed by the LeBail method and the parameters are as follows: a=18.944(7) Å, b=13.400(3) Å, c=10.422(2) Å, α=89.38(2), β=123.44(2), γ=103.36(2°) and volume=2126 (1) Å 3.

This crystalline form of valbenazine ditosylate was also subjected to DSC, TGA, and DVS. The DSC analysis, shown in FIG. 6, shows a first endothermic phenomenon at 104° C. with an associated heat of 56.9 J/g, a second endothermic phenomenon at 150° C. with an associated heat of 9.2 J/g and a third endothermic phenomenon at 235° C. with an associated heat of 0.9 J/g and a weight loss of 2.7% from 30° C. to 149° C. observed in a TGA analysis, as shown in FIG. 7. DVS analysis at 25° C. in the first cycle shows water sorption by the sample up to approximately 1.4% at 90% relative humidity, only in the first step a sorption/desorption phenomenon around 70% of RH is observed which can be associated to a recrystallization from amorphous.

Figure 11:
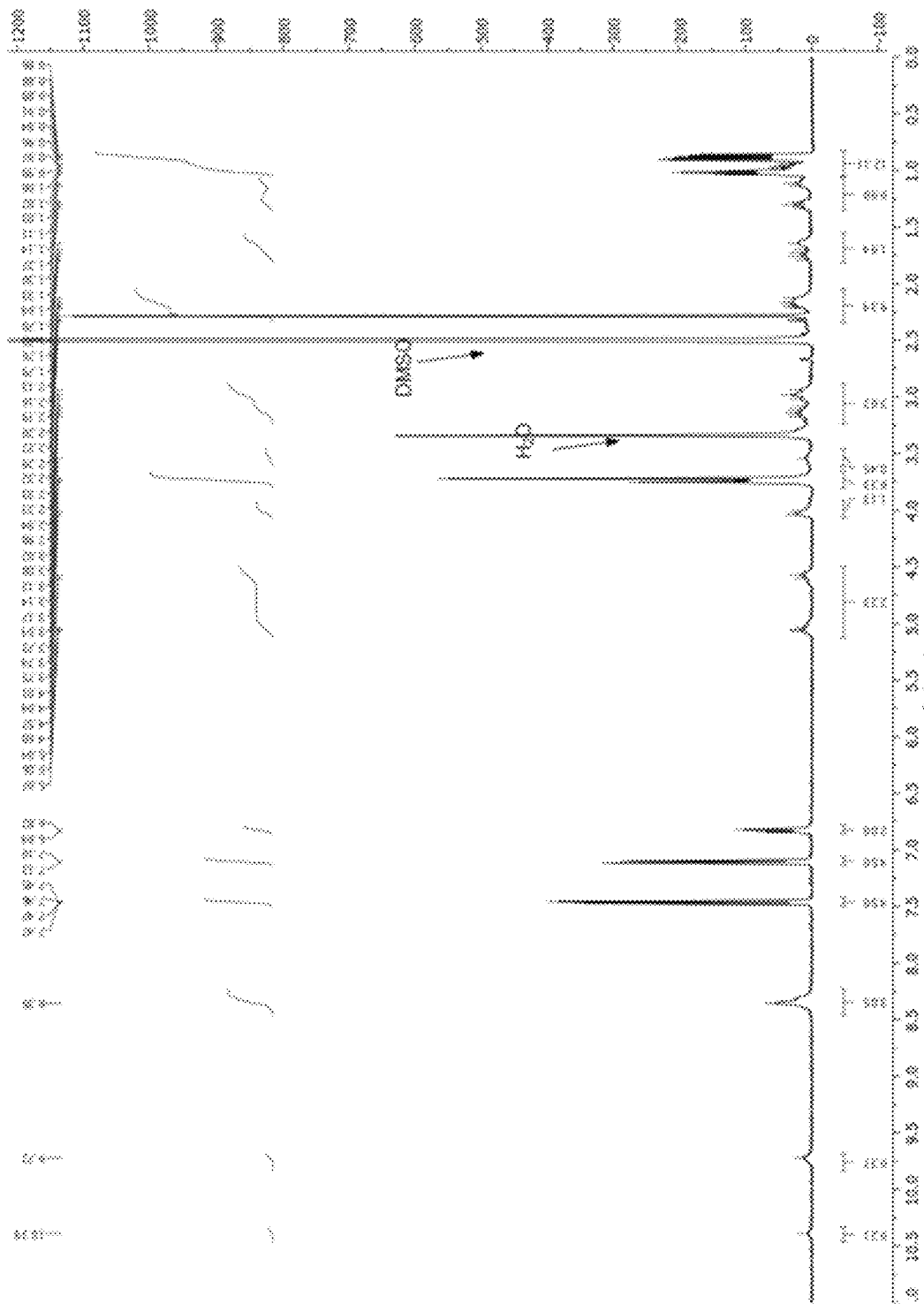
FIG. 11 shows a $H^1$ NMR spectrum of Form E of valbenazine ditosylate.

The crystalline valbenazine ditosylate of this example was also analyzed by NMR. To the extent any $CHCl_3$ was present, it was below the limit of detection. The NMR analysis, shown in FIG. 11, also confirms it to be a crystalline valbenazine ditosylate hydrate with a stoichiometry API:$H_2O$ ratio of 1:1.

Example 4

Preparation of Form F Valbenazine Ditosylate

A valbenazine methanolic solution obtained according to preparative example 1 was concentrated. Chloroform (120 ml, 12 vol) was added at room temperature. p-toluenesulfonic acid (11.9 grams, 0.064 mol, 2 eq) and water (10 ml, 1 vol) were added and the mixture was heated to reflux until complete dissolution. After that, the mixture was slow cooled, and a sample was taken when the mixture had cooled to a temperature of approximately 30° C. The sample was filtered and washed with chloroform. The product was then dried under vacuum at 60° C. for 5 hours to obtain crystalline valbenazine ditosylate. The crystalline valbenazine ditosylate was then characterized by XRPD as Form F, having a XRPD pattern as depicted in FIG. 9 which at least the following peaks, expressed in degrees 2-theta: 5.5, 5.8, 6.8, 10.3, 15.4, 15.9, 17.0, 18.0, 18.6 and 19.7±0.2 degrees 2-theta.

Figure 12:
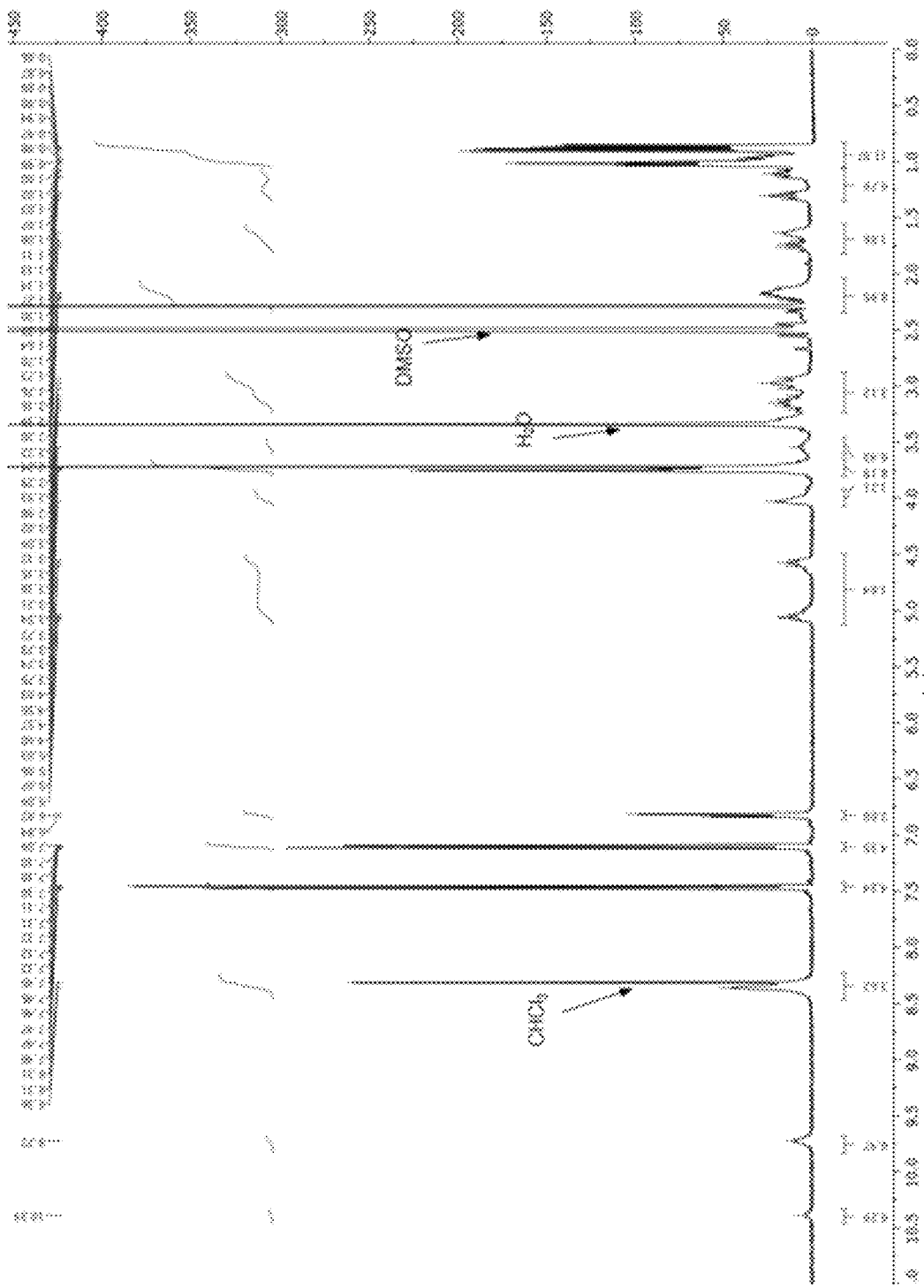
FIG. 12 shows a $H^1$ NMR spectrum of Form F of valbenazine ditosylate.

The crystalline valbenazine ditosylate of this example was also analyzed by NMR. The results, shown in FIG. 12, confirm it to be a chloroform solvate of valbenazine ditosylate.

What is claimed is:

1. Crystalline valbenazine ditosylate having an X-ray powder diffractogram pattern comprising peaks at 2-theta angles of 6.1, 16.9, 17.2, 19.1 and 19.6±0.2 degrees 2-theta.

2. The crystalline valbenazine ditosylate of claim 1, having an X-ray powder diffractogram pattern essentially the same as shown in FIG. 1.

3. The crystalline valbenazine ditosylate of claim 1, having at least one of the following:
   a) a differential scanning calorimetry curve essentially the same as shown in FIG. 2, when measured at a heating rate of 10° C./min;
   b) a TGA essentially the same as shown in FIG. 3, when measured at a rate of 1° C./min; or
   c) a DVS essentially the same as shown in FIG. 4, when measured with a method using two cycles (0% to 90% RH) and (90% to 0% RH).

4. Crystalline valbenazine ditosylate having an X-ray powder diffractogram pattern comprising peaks at 2-theta angles of 5.8, 6.8, 15.9, 17.0 and 18.6±0.2 degrees 2-theta.

5. The crystalline valbenazine ditosylate of claim 4, having an X-ray powder diffractogram pattern essentially the same as shown in FIG. 5.

6. The crystalline valbenazine ditosylate of claim 5, having at least one of the following:
   a) a differential scanning calorimetry curve essentially the same as shown in FIG. 6, when measured at a heating rate of 10° C./mm;
   b) a TGA essentially the same as shown in FIG. 7, when measured at a rate of 10° C./min; or
   c) a DVS essentially the same as shown in FIG. 8, when measured with a method using two cycles (0% to 90% RH) and (90% to 0% RH).

7. A pharmaceutical composition comprising the crystalline ditosylate of claim 1, and one or more pharmaceutically acceptable excipients.

8. The pharmaceutical composition of claim 7, which is an oral solid dosage form.

9. A pharmaceutical composition comprising the crystalline ditosylate of claim 4, and one or more pharmaceutically acceptable excipients.

10. The pharmaceutical composition of claim 9, which is an oral solid dosage form.

11. A method for the treatment of one or more symptoms of hyperkinetic disorder, and preferably drug-induced tardive dyskinesia and Tourette's syndrome, comprising administering the crystalline valbenazine ditosylate of claim 1.

12. A method for the treatment of one or more symptoms of hyperkinetic disorder, and preferably drug-induced tardive dyskinesia and Tourette's syndrome, comprising administering the crystalline valbenazine ditosylate of claim 4.

13. A method for inhibiting vesicular monoamine transporter isoform 2 in a subject comprising administering to the subject the crystalline valbenazine ditosylate of claim 1.

14. A method for inhibiting vesicular monoamine transporter isoform 2 in a subject comprising administering to the subject the crystalline valbenazine ditosylate of claim 4.

15. A process for the preparation of the crystalline valbenazine ditosylate of claim 1 comprising:
   (i) reacting valbenazine with p-toluenesulfonic acid monohydrate in dichloromethane at room temperature;
   (ii) slurrying the reaction mixture of step (i);
   (iii) filtering the organic layer from the slurry at room temperature;
   (iv) obtaining a solid product; and
   (iv) drying the solid product under vacuum.

16. A process for the preparation of crystalline valbenazine ditosylate of claim 4 comprising:
   (i) reacting valbenazine with p-toluenesulfonic acid monohydrate in chloroform at a temperature from about 45° C. to about 60° C.;
   (ii) slurrying the reaction mixture of step (i);
   (iii) filtering the organic layer from the slurry at room temperature;
   (iv) obtaining a solid product; and
   (iv) drying the solid product under vacuum.

17. Crystalline valbenazine ditosylate having an X-ray powder diffractogram pattern comprising peaks at 2-theta angles of 5.5, 5.8, 6.8, 10.3, 15.4, 15.9, 17.0, 18.0, 18.6 and 19.7±0.2 degrees 2-theta.

18. The crystalline valbenazine ditosylate of claim 13, having an X-ray powder diffractogram pattern essentially the same as shown in FIG. 9.

19. The crystalline valbenazine ditosylate of claim 1, where the crystalline valbenazine ditosylate is in the form of a dichloromethane solvate.

20. The crystalline valbenazine ditosylate of claim 4, where the crystalline valbenazine ditosylate is in the form of a hydrate.

21. The crystalline valbenazine ditosylate of claim 17, where the crystalline valbenazine ditosylate is in the form of a chloroform solvate.

22. The pharmaceutical composition of claim 7, where the crystalline valbenazine ditosylate is in the form of a dichloromethane solvate.

23. The pharmaceutical composition of claim 9, where the crystalline valbenazine ditosylate is in the form of a hydrate.

24. The method of claim 11, where the crystalline valbenazine ditosylate is in the form of a dichloromethane solvate.

25. The method of claim 12, where the crystalline valbenazine ditosylate is in the form of a hydrate.

26. The method of claim 13, where the crystalline valbenazine ditosylate is in the form of a dichloromethane solvate.

27. The method of claim 14, where the crystalline valbenazine ditosylate is in the form of a hydrate.

* * * * *